United States Patent [19]

Takahoso et al.

[11] Patent Number: 5,179,221

[45] Date of Patent: Jan. 12, 1993

[54] METHOD FOR PRODUCTION OF 3-CYANO-3,5,5-TRIMETHYL CYCLOHEXANONE

[75] Inventors: Hiroshi Takahoso, Mobara; Norio Takahashi, Ichinomiya; Koji Midorikawa, Mobara; Toshiyasu Sato, Ichinomiya, all of Japan

[73] Assignee: Nippon Chemicals Co., Ltd., Tokyo, Japan

[21] Appl. No.: 727,447

[22] Filed: Jul. 9, 1991

[30] Foreign Application Priority Data

Mar. 5, 1991 [JP] Japan .................... 3-38197

[51] Int. Cl.$^5$ .................. C07C 253/10; C07C 253/30
[52] U.S. Cl. ........................................... 558/341
[58] Field of Search ..................................... 558/341

[56] References Cited

U.S. PATENT DOCUMENTS

| | | | |
|---|---|---|---|
| 4,299,775 | 11/1981 | Dubreux | 558/341 |
| 5,011,968 | 4/1991 | Thunberg et al. | 558/341 |

FOREIGN PATENT DOCUMENTS

| | | | |
|---|---|---|---|
| 1085871 | 7/1960 | Fed. Rep. of Germany . | |
| 1240854 | 5/1967 | Fed. Rep. of Germany | 558/341 |
| 407486 | 4/1965 | Japan . | |
| 0116038 | 7/1982 | Japan | 558/341 |
| 625418 | 7/1982 | Japan . | |
| 61-33157 | 2/1986 | Japan . | |
| 61-33158 | 2/1986 | Japan . | |
| 62-164656 | 7/1987 | Japan . | |
| 147459 | 10/1989 | Japan . | |
| 887413 | 1/1962 | United Kingdom . | |

OTHER PUBLICATIONS

J. Org. Chem. 13, 31–37 (1948), Whitmore, et al.
J. Am. Chem. Soc. 104, 6449–6450 (1982), Ito, et al.
CA 97:215625w Nitto Chem Ind. (1982).
WPI Abs. abstracting JP-B-62-5418 (no date present).
CA 56:4639f, Rohm & Haas Co. (1962).
CA 109:92347p Hirako (1988).

*Primary Examiner*—Joseph Paul Brust
*Attorney, Agent, or Firm*—Gordon W. Hueschen

[57] ABSTRACT

A method for the production of 3-cyano-3,5,5-trimethyl cyclohexanone by the reaction of isophorone with hydrogen cyanide in the presence of a quaternary ammonium salt or quaternary phosphonium salt and a basic compound as a catalyst in the form dissolved or dispersed in water or in the absence of water, which method comprises effecting said reaction by using said quaternary ammonium salt or quaternary phosphonium salt in an amount in the range of from 0.001 to 0.1 mol per mol of isophorone and said basic compound and in an amount in the range of from 0.5 to 3.0 mols per mol of said quaternary ammonium salt or quaternary phosphonium salt and, when water is used, using water in an amount in the range of 0.1 to 25% by weight based on the amount of isophorone and introducing hydrogen cyanidehydrocyanic acid at a ratio in the range of from 0.6 to 1.0 mol per mol of isophorone at a temperature in the range of from 90° to 140° C.

5 Claims, No Drawings

METHOD FOR PRODUCTION OF 3-CYANO-3,5,5-TRIMETHYL CYCLOHEXANONE

BACKGROUND OF THE INVENTION

1. Field of the Invention

This invention relates to a method for the production of 3-cyano-3,5,5-trimethyl cyclohexanone. More particularly, it relates to a method for producing 3-cyano-3,5,5-trimethyl cyclohexanone in a stoichiometric yield by the reaction of isophorone with hydrogen cyanide under specific conditions in the presence of a quaternary ammonium salt or a quaternary phosphonium salt and a basic compound.

2. Description of the Prior Art

3-Cyano-3,5,5-trimethyl cyclohexanone is an industrially useful and important compound which, through hydrogenation and amination, produces 1-amino-3-aminomethyl-3,5,5-trimethyl cyclohexane to be used as a curing agent for epoxy resin and, further through isocyanation, produces 3-isocyanate methyl-3,5,5-trimethyl cyclohexyl-1-isocyanate to be used as a raw material for polyurethane coating material attracting attention especially for use in automobiles, powder coating material, quality elastomer, and leather surface treating agent.

It has been known to the art to produce 3-cyano-3,5,5-trimethyl cyclohexanone from isophorone and hydrogen cyanide or a cyanide as raw materials. By the method disclosed in J. Org. Chem., Vol. 13, pp. 31 to 37 (1948), for example, 3-cyano-3,5,5-trimethyl cyclohexanone is synthesized in a yield of 60% by one week reaction of isophorone with sodium cyanide at normal room temperature in a mixed solution of methanol, water, and acetic acid. It is self-evident, however, that this method is least feasible as a commercial process because it has low productivity and requires a time-consuming reaction. By the method disclosed in J. Am. Chem. Soc., Vol. 104, No. 23, pp. 6,449 and 6,450 (1982), 3-cyano-3,5,5-trimethyl cyclohexanone is synthesized in a yield of 63% by causing isophorone to react with t-butyl isocyanide in the presence of titanium tetrachloride of an amount substantially equimolar to the isophorone. This method has poor commercial feasibility because it suffers from poor productivity and necessitates use of expensive raw materials.

West German Patent No. 1,085,871 discloses a method for synthesizing 3-cyano-3,5,5-trimethyl cyclohexanone by causing isophorone to react with hydrogen cyanide in a polar solvent such as, for example, dimethyl acetamide in the presence of an alkali metal salt as a catalyst. British Patent No. 887,413 discloses a method for synthesizing 3-cyano-3,5,5-trimethyl cyclohexanone by causing isophorone to react with potassium cyanide in such a polar solvent as dimethyl acetamide. These methods are incapable of serving satisfactorily as commercial processes because they produce 3-cyano-3,5,5-trimethyl cyclohexanone only in a low yield of about 70% and call for an unduly large load in the recovery of a used solvent.

Further, Japanese Patent Publication SHO 40(1965)-7,486 discloses a method for continuously synthesizing 3-cyano-3,5,5-trimethyl cyclohexanone by supplying to an alkaline catalyst deposited on a solid carrier a gaseous isophorone-hydrogen cyanide mixture having a hydrogen cyanide content of not more than about 10% by weight based on isophorone. This method, however, is a problematic process from the commercial point of view because the catalyst is inevitably poisoned by the by-produced polymer of hydrogen cyanide and prevented from offering an appreciably long service life and the reaction entails recovery of a large amount of unaltered isophorone.

West German Patent No. 1,240,854 discloses a method for synthesizing 3-cyano-3,5,5-trimethyl cyclohexanone by causing isophorone to react with hydrogen cyanide in the presence of an alkali metal salt as a catalyst with methanol used as a dispersant for the catalyst. When this method was replicated, however, it was found that the reaction produced 3-cyano-3,5,5-trimethyl cyclohexane only in a low yield of about 70% and entailed by-production of a large amount of polymer of hydrogen cyanide. Thus, this method is problematic as a commercial process.

Japanese Patent Publication SHO 62(1987)-5,418 discloses a method for synthesizing 3-cyano-3,5,5-trimethyl cyclohexanone by causing hydrogen cyanide to react with a large excess of isophorone enough to preclude by-production of polymer of hydrogen cyanide in the presence of an inorganic basic catalyst and a glycol. When this method was replicated, however, it was found to be a commercially problematic process because it produced 3-cyano-3,5,5-trimethyl cyclohexanone only in a low yield of about 80% and necessitated recovery of a large amount of an unaltered isophorone.

Japanese Patent Publication HEI 1(1989)-47,459 discloses a method for synthesizing 3-cyano-3,5,5-trimethyl cyclohexanone by causing isophorone to react in a two-phase system with sodium cyanide or potassium cyanide dissolved as a cyanide in water in the presence of a phase transfer catalyst selected from among quaternary ammonium salts and quaternary phosphonium salts. This method, however, is not fully satisfactory because the conversion of isophorone is low in spite of the use of the cyanide in a large excess relative to isophorone, the amount of an unaltered isophorone to be recovered is consequently large, and the selectivity of the reaction for 3-cyano-3,5,5-trimethyl cyclohexanone is only about 90%. Since this method uses the solvent, it requires the solvent to be recovered from the reaction mixture. It further abhors use of hydrogen cyanide on account of the by-production of a polymer of hydrogen cyanide and the operational difficulty encountered in the use of this acid and resorts inevitably to use of sodium cyanide or potassium cyanide as a cyanide. In actuality, this cyanide is used in a very large excess falling in the range of from 1 to 10 mols per mol of isophorone. In this method, the cyanide remains in an unaltered form in a large amount after completion of the reaction and poses a difficult problem of handling. The patent publication has no clear mention about the solution of this problem. It may be added that when sodium cyanide or potassium cyanide dissolved in water is used as a cyanide as clearly mentioned in the patent publication, the alkalinity of the aqueous phase of the reaction system increases with the progress of the reaction. The reaction, therefore, entails a secondary operation of buffering the reaction system with an acid. In the light of these problems, this method does not deserve adoption as a commercial process.

Japanese Patent Laid-Open SHO 61(1986)-33,157 discloses a method for synthesizing 3-cyano-3,5,5-trimethyl cyclohexanone in a yield of about 95% by causing isophorone to react with hydrogen cyanide in the presence of a quaternary ammonium hydroxide or a quaternary phosphonium hydroxide. By this method, however, since the quaternary ammonium hydroxide or quaternary phosphonium hydroxide has strong basicity, such secondary reactions as the polymerization of hydrogen cyanide and such secondary reactions as the decomposition and polymerization of 3-cyano-3,5,5-trimethyl cyclohexanone formed during the course of the reaction are not easily repressed. The reaction, therefore, entails by-production of the polymer in a large amount and necessitates a difficult after-treatment. This method is also incapable of serving satisfactorily as a commercial process of the kind aimed at by the present inventors.

Japanese Patent Laid-Open SHO 61(1986)-33,158 discloses a method for synthesizing 3-cyano-3,5,5-trimethyl cyclohexanone by causing isophorone to react with hydrogen cyanide in the presence of a diazabicycloalkene as a catalyst. This method has the disadvantage that the catalyst to be used is expensive and the spent catalyst is not easily recovered for cyclic use and, because of the strong basicity of the catalyst, the reaction entails by-production of the polymer in a large amount. Thus, this method has much room for further improvement.

Inherently, hydrogen cyanide exhibits very low addition reactivity to the double bond of isophorone. Numerous measures, therefore, have been proposed as described above for the purpose of increasing the cyan ion concentration in the organic layer containing isophorone and consequently enhancing the reactivity of the reaction system. None of these methods, however, deserve to be called a fully satisfactory commercial process in terms of economy, productivity, operational efficiency, etc.

An object of this invention, therefore, is to provide a novel method for the production of 3-cyano-3,5,5-trimethyl cyclohexanone.

Another object of this invention is to provide a method for producing 3-cyano-3,5,5-trimethyl cyclohexanone in a stoichiometric yield while using hydrogen cyanide and yet precluding by-production of the polymer of hydrogen cyanide, obviating the necessity of using a solvent for solubilizing or dispersing a catalyst in isophorone, or requiring use of a large excess of either isophorone or a cyanide and consequently entailing recovery of a large amount of an unaltered raw material.

SUMMARY OF THE INVENTION

The objects of this invention described above are accomplished by a method for the production of 3-cyano-3,5,5-trimethyl cyclohexanone by the reaction of isophorone with hydrogen cyanide in the presence of a quaternary ammonium salt or a quaternary phosphonium salt and a basic compound used as a catalyst in the form dissolved or dispersed in water or in the absence of water, which method effects the production of 3-cyano-3,5,5-trimethyl cyclohexanone by selecting the amount of the quaternary ammonium salt or quaternary phosphonium salt in the range of from 0.001 to 0.1 mol per mol of isophorone and the amount of the basic compound in the range of 0.5 to 3.0 mols per mol of the quaternary ammonium salt or quaternary phosphonium salt and, when water is used, selecting the amount of water in the range of from 0.1 to 25% by weight based on the amount of isophorone and causing the reaction by introducing hydrogen cyanide in a ratio in the range of 0.6 to 1.0 mol per mol of isophorone at a temperature in the range of 90° to 140° C.

The present invention is further directed to a method for the production of 3-cyano-3,5,5-trimethyl cyclohexanone, which method comprises causing the resultant reaction solution to contact water thereby separating the reaction solution into an organic layer and an aqueous layer containing the quaternary ammonium salt or quaternary phosphonium salt and the basic compound used in the reaction and recovering from the separated aqueous layer the quaternary ammonium salt or quaternary phosphonium salt and the basic compound and recycling the recovered catalyst to the next cycle of the reaction.

Since this invention utilizes the reaction of isophorone with hydrogen cyanide under specific conditions in the presence of a specific quaternary ammonium salt or quaternary phosphonium salt and a basic compound, it allows 3-cyano-3,5,5-trimethyl cyclohexanone to be produced in a stoichiometric yield very easily while using hydrogen cyanide and yet precluding such secondary reaction as polymerization of hydrogen cyanide without requiring use of a large amount of solvent, and obviating the necessity for using a large excess of either isophorone or a cyanide compound and consequently recovering a large amount of an unaltered raw material. Thus, this invention has an effect of allowing advantageous production of 3-cyano-3,5,5-trimethyl cyclohexanone as an industrially useful and important compound.

EXPLANATION OF THE PREFERRED EMBODIMENT

This invention, as described above, comprises producing 3-cyano-3,5,5-trimethyl cyclohexanone by causing isophorone to react with hydrogen cyanide under specific conditions in the presence of a specific quaternary ammonium salt or quaternary phosphonium salt and a basic compound as a catalyst.

The quaternary ammonium salts which are advantageously usable in this invention are represented by the following general formula (1).

$$R^1(R^2)_3 NX \qquad (1)$$

wherein $R^1$ is benzyl group or alkyl group of 1 to 4 carbon atoms, $R^2$ is alkyl group of 1 to 4 carbon atoms, and X is chlorine atom, bromine atom, or iodine atom.

Typical examples of the quaternary ammonium salt of the general formula (1) are tetraalkyl quaternary ammonium salts such as tetramethyl ammonium chloride, tetramethyl ammonium bromide, tetramethyl ammonium iodide, tetraethyl ammonium chloride, tetraethyl ammonium bromide, tetraethyl ammonium iodide, tetra-n-propyl ammonium chloride, tetra-n-propyl ammonium bromide, tetra-n-propyl ammonium iodide, tetra-n-butyl ammonium chloride, tetra-n-butyl ammonium bromide, tetra-n-butyl ammonium iodide, methyltriethyl ammonium chloride, methyltriethyl ammonium bromide, methyltriethyl ammonium iodide, and propyltriethyl ammonium chloride and benzyltrialkyl quaternary ammonium salts such as benzyltrimethyl ammonium chloride, benzyltrimethyl ammonium bromide, benzyltrimethyl ammonium iodide, benzyltriethyl ammonium chloride, benzyltriethyl ammonium bromide, and benzyltriethyl ammonium iodide. Among other quaternary ammonium salts cited above, tetramethyl ammonium chloride, tetramethyl ammonium bromide, tetraethyl ammonium chloride, tetraethyl ammonium bromide, methyltriethyl ammonium chloride, and methyltriethyl ammonium bromide prove to be particularly preferable.

The quaternary phosphonium salts which are advantageously usable in this invention are represented by the following general formula (2).

$$R^1(R^2)_3 PX \qquad (2)$$

wherein $R^1$ is benzyl group or alkyl group of 1 to 4 carbon atoms, $R^2$ is alkyl group of 1 to 4 carbon atoms, and X is chlorine atom, bromine atom, or iodine atom.

Typical examples of the quaternary phosphonium salt of the general formula (2) are tetraalkyl quaternary phosphonium salts such as tetramethyl phosphonium chloride, tetramethyl phosphonium bromide, tetramethyl phosphonium iodide, tetraethyl phosphonium chloride, tetraethyl phosphonium bromide, tetraethyl phosphonium iodide, tetra-n-propyl phosphonium chloride, tetra-n-propyl phosphonium bromide, tetra-n-propyl phosphonium iodide, tetra-n-butyl phosphonium chloride, tetra-n-butyl phosphonium bromide, tetra-n-butyl phosphonium iodide, methyltriethyl phosphonium chloride, methyltriethyl phosphonium bromide, methyltriethyl phosphonium iodide, and propyltriethyl phosphonium chloride and benzyltrialkyl quaternary phosphonium salts such as benzyltrimethyl phosphonium chloride, benzyltrimethyl phosphonium bromide, benzyltrimethyl phosphonium iodide, benzyltriethyl phosphonium chloride, benzyltriethyl phosphonium bromide, and benzyltriethyl phosphonium iodide.

The basic compounds which are effectively usable in the present invention include carbonates, hydrogencarbonates, hydroxides, cyanides, oxides, lower fatty acid salts, having 1-5 carbon atoms, and alcoholates of alkali metals or alkaline earth metals. Among other basic compounds cited above, sodium carbonate, potassium carbonate, sodium hydrogen carbonate, and potassium hydrogen carbonate prove to be particularly preferable.

In the production of 3-cyano-3,5,5-trimethyl cyclohexanone by the reaction of isophorone with hydrogen cyanide in accordance with this invention, the quaternary ammonium salt or quaternary phosphonium salt is used in combination with the basic compound as a catalyst. Preferably at least one quaternary ammonium salt selected from the group consisting of tetramethyl ammonium chloride, tetramethyl ammonium bromide, tetraethyl ammonium chloride, tetraethyl ammonium bromide, methyltriethyl ammonium chloride, and methyltriethyl ammonium bromide is used in combination with at least one basic compound selected from the group consisting of sodium carbonate, potassium carbonate, sodium hydrogen carbonate, and potassium hydrogen carbonate.

The proportion of the quaternary ammonium salt or quaternary phosphonium salt to be used as the catalyst in the present invention is in the range of from 0.001 to 0.1 mol, preferably from 0.02 to 0.07 mol, per mol of isophorone. If this proportion is less than 0.001 mol, the reaction does not proceed sufficiently. Conversely, if the proportion exceeds 0.1 mol, the excess is wasted without bringing about a proportionate increase in its effect.

The amount of the basic compound to be used is in the range of from 0.5 to 3.0 mols per mol of the quaternary ammonium salt or quaternary phosphonium salt. If this amount is less than 0.5 mol, the reaction of isophorone with hydrogen cyanide does not proceed sufficiently. Conversely, if this amount exceeds 3.0 mols, the excess is wasted without producing a proportionate increase in its effect.

The catalyst for the reaction of this invention is used in a form dissolved or dispersed in water or in the absence of water. Preferably, it is used as dissolved or dispersed in water. The amount of this water preferably is in the range of 0.1 to 25% by weight based on the amount of isophorone. If this amount exceeds 25% by weight, the excess not only fails to bring about a proportionate increase in its effect but also renders difficult the maintenance of the reaction temperature at the prescribed level and interferes with normal progress of the reaction.

In this invention, the reaction and the after treatment can be carried out without use of any organic solvent. An organic solvent, when necessary, may be used therefor. The organic solvents which are advantageously usable herein include aliphatic hydrocarbons, aromatic hydrocarbons, and halogenated hydrocarbons, for example.

The proportion of hydrogen cyanide to be used in the present invention is in the range of from 0.6 to 1.0 mol, preferably from 0.65 to 0.85 mol, per mol of isophorone. If the proportion of hydrogen cyanide is less than 0.6 mol, the amount of an unaltered isophorone is so large as to not only lower the productivity of the reaction but also aggravate the load exerted on the recovery of the unaltered isophorone. Conversely, if this proportion exceeds 1.0 mol, the greater part of the excess of hydrogen cyanide goes to form a polymer, makes no contribution to the reaction aimed at, fails to bring about a proportionate increase in its effect, gives rise to an unwanted by-product, and renders difficult the after-treatment of the reaction solution.

The reaction temperature in this invention is in the range of from 90° to 140° C., preferably from 100° to 130° C. If this reaction temperature is lower than 90° C., the reaction of isophorone with hydrogen cyanide for consequent formation of 3-cyano-3,5,5-trimethyl cyclohexanone is initiated only with difficulty. Conversely, if this reaction temperature exceeds 140° C., the secondary reaction to polymerize hydrogen cyanide is accelerated so much as to degrade the yield of the reaction.

The time for the introduction of hydrogen cyanide in the reaction of the present invention is in the range of from one to seven hours, preferably from two to four hours. If this time of introduction is less than one hour, the reaction proceeds vigorously and evolves heat so much as to render difficult the control of the reaction temperature at the prescribed level. Further, the introduced hydrogen cyanide fails to react instantaneously and partly remains in an unaltered form and, even when the reaction system is left aging after the introduction of hydrogen cyanide, part of the hydrogen cyanide is lost by the secondary reaction such as polymerization and consequently suffered to degrade the yield of the product. Conversely, if this time of introduction exceeds seven hours, the excess of time not only fails to bring about a proportionate increase in its effect but also compels the formed 3-cyano-3,5,5-trimethyl cyclohexanone to undergo gradual loss by inducing a secondary reaction under the ambience of reaction and consequently degrades the yield of the reaction product.

The reaction described above is carried out as follows.

The isophorone, and the quaternary ammonium salt or quaternary phosphonium salt and the basic compound which are dissolved or dispersed in water, are mixed. The resultant mixture heated to the prescribed reaction temperature is kept at this temperature and, at the same time, the hydrogen cyanide in a liquid phase or a gaseous phase is introduced into the heated mixture and allowed to react therein. Though the reaction is nearly completed immediately after the introduction of the hydrogen cyanide, it is preferable to be completed by allowing the reaction solution to age by being maintained at the prescribed reaction temperature. Preferably, this aging time is in the range of from 0.01 to four hours, preferably from 0.5 to two hours. If the aging time is unduly long, the excess of aging time has an adverse effect of promoting the unwanted secondary reaction of the formed 3-cyano-3,5,5-trimethyl cyclohexanone under the ambience of the reaction.

After the reaction is completed, for the purpose of separating from the resultant reaction solution the quaternary ammonium salt or quaternary phosphonium salt and the basic compound as the catalyst, the reaction solution is separated by contact with water into an organic layer and an aqueous layer containing the quaternary ammonium salt or quaternary phosphonium salt and the basic compound. From the separated aqueous layer containing the quaternary ammonium salt or quaternary phosphonium salt and the basic compound, the quaternary ammonium salt or quaternary phosphonium salt and the basic compound are recovered and put to reuse in the next cycle of the reaction.

While the greater part of the catalyst can be separated by the treatment mentioned above, part of the catalyst remains in the organic layer and imparts alkalinity. When the organic layer is distilled without any treatment for the extraction of 3-cyano-3,5,5-trimethyl cyclohexanone therefrom, the heat of the distillation induces loss of 3-cyano-3,5,5-trimethyl cyclohexanone through secondary reaction. To preclude this trouble, the organic layer is neutralized with an acid to impart acidity and stabilize 3-cyano-3,5,5-trimethyl cyclohexanone.

From the organic layer obtained in consequence of the treatment described above, unaltered isophorone is recovered and the produced 3-cyano-3,5,5-trimethyl cyclohexanone is obtained. This process is generally effected by vacuum distillation. The 3-cyano-3,5,5-trimethyl cyclohexanone obtained by the ordinary distillation possesses sufficient purity and endures normal use. When it is desired to possess still higher purity, it may be refined by recrystallization from hexane or isopropanol. The isophorone which is separated during the distillation can be directly reused for the next cycle of the reaction.

Now, this invention will be described more specifically below with reference to working examples. It should be noted, however, that this invention is not limited to the examples.

EXAMPLE 1

In a 300 ml round-bottomed flask equipped with a mechanical stirrer, a thermometer, a reflux condenser and a cooling dropping funnel, 138.2 g (1.0 mol) of isophorone, 6.9 g (0.033 mol) of tetraethyl ammonium bromide, 6.9 g (0.050 mol) of potassium carbonate and 13.8 g of water were placed and stirred. The well-stirred mixture was heated to 110° C. and 18.9 g (0.70 mol) of hydrogen cyanide was added dropwise at a temperature of 110° C. over a period of three hours. And then, the reaction mixture was aged at 110° C. for one hour. After the completion of the reaction, the resultant reaction mixture was cooled to 50° C. The reaction mixture was washed with 70 g of water for catalyst removal and then with 70 g of 6% nitric acid for neutralization. Analysis by means of gas chromatography showed that 114.5 g (0.693 mol) of 3-cyano-3,5,5-trimethyl cyclohexanone was formed and 40.5 g of unaltered isophorone was remained. Thus, the yield of 3-cyano-3,5,5-trimethyl cyclohexanone was 99% based on hydrogen cyanide and selectivity expressed by the molar ratio of 3-cyano-3,5,5-trimethyl cyclohexanone formed to isophorone converted was 98%. When the washed reaction mixture was distilled, there were obtained 40.8 g of the recovered isophorone (containing 39.6 g of isophorone and 1,2 g of 3-cyano-3,5,5-trimethyl cyclohexanone) and 113.2 g of 3-cyano-3,5,5-trimethyl cyclohexanone having a purity of 99%.

EXAMPLE 2

When the catalyst-containing aqueous layer obtained in Example 1 was analyzed by titration, it was found to contain 6.2 g of tetraethyl ammonium bromide and 6.2 g of potassium carbonate. Thus, the recovery ratios of the compounds were each 90% based on the initially charged amounts. In the same reaction apparatus as used in Example 1, the aforementioned aqueous layer concentrated to 29.0 g, 40.8 g of the recovered isophorone in Example 1 (comprising 39.6 g of isophorone and 1.2 g of 3-cyano-3,5,5-trimethyl cyclohexanone), 98.6 g of isophorone, 0.7 g of tetraethyl ammonium bromide, and 0.7 g of potassium carbonate were placed and, by following the procedure of Example 1, 18.9 g of hydrogen cyanide was added thereto and left reacting therein. When the organic layer obtained by aftertreating the resultant reaction mixture was analyzed by gas chromatography, it was found to contain 115.9 g of 3-cyano-3,5,5-trimethyl cyclohexanone as the product and 40.1 g of an unaltered isophorone. Thus, the yield of 3-cyano-3,5,5-trimethyl cyclohexanone minus the part originating from the recovered isophorone based on hydrogen cyanide was 99% and the selectivity of the reaction (based on the converted isophorone) was 98%. When the organic phase thus obtained was distilled, there were obtained 40.6 g of recovered isophorone (comprising 39.2 g of isophorone and 1.4 g of 3-cyano-3,5,5-trimethyl cyclohexanone) and 115.7 g of 3-cyano-3,5,5-trimethyl cyclohexanone having a purity of 99%.

EXAMPLE 3

By following the procedure of Example 2, the recovery and reuse of tetraethyl ammonium bromide and potassium carbonate as the catalyst was repeated a total of eight cycles. The recovery ratio of tetraethyl ammonium bromide ranged between 87 and 92% and that of potassium carbonate between 85 to 91%. In each of the subsequent cycles, tetraethyl ammonium bromide and potassium carbonate were replenished to the respectively prescribed levels. The yields of 3-cyano-3,5,5-trimethyl cyclohexanone (based on hydrogen cyanide) ranged between 98 and 99% and the selectivities of the reaction (based on the converted isophorone) between 97 and 98%.

EXAMPLE 4

The procedure of Example 1 was repeated, except that 21.6 g (0.80 mol) of hydrogen cyanide was used instead. The resultant reaction solution was subjected to aftertreatment. When the organic layer consequently obtained was analyzed by gas chromatography, it was found to contain 128.2 g (0.776 mol) of 3-cyano-3,5,5-trimethyl cyclohexanone and 28.6 g of unaltered isophorone. Thus, the yield of 3-cyano-3,5,5-trimethyl cyclohexanone (based on hydrogen cyanide) was 97% and the selectivity of the reaction (based on the converted isophorone) was 98%.

EXAMPLE 5

The procedure of Example 1 was repeated, except that 3.6 g (0.033 mol) of tetramethyl ammonium chloride was used in the place of tetraethyl ammonium bromide. The resultant reaction solution was subjected to after treatment. When the organic layer consequently obtained was analyzed by gas chromatography, it was found to contain 111.9 g (0.677 mol) of 3-cyano-3,5,5-trimethyl cyclohexanone and 43.5 g of unaltered isophorone. Thus, the yield of 3-cyano-3,5,5-trimethyl cyclohexanone (based on hydrogen cyanide) was 97f% and the selectivity of the reaction (based on the converted isophorone) was 99%.

EXAMPLE 6

The procedure of Example 1 was repeated, except that 6.5 g (0.033 mol) of methyltriethyl ammonium bromide was used in the place of tetraethyl ammonium bromide. The resultant reaction solution was subjected to aftertreatment. When the organic layer consequently obtained was analyzed by gas chromatography, it was found to contain 112.1 g (0.678 mol) of 3-cyano-3,5,5-trimethyl cyclohexanone and 39.6 g of unaltered isophorone. Thus, the yield of 3-cyano-3,5,5-trimethyl cyclohexanone (based on hydrogen cyanide) was 97% and the selectivity of the reaction (based on the converted isophorone) was 95%.

EXAMPLE 7

The procedure of Example 1 was repeated, except that 6.0 g (0.033 mol) of tetraethyl ammonium chloride was used in the place of tetraethyl ammonium bromide. The resultant reaction solution was subjected to after-treatment. When the organic layer consequently obtained was analyzed by gas chromatography, it was found to contain 113.5 g (0.687 mol) of 3-cyano-3,5,5-trimethyl cyclohexanone and 41.4 g of unaltered isophorone. Thus, the yield of 3-cyano-3,5,5-trimethyl cyclohexanone (based on hydrogen cyanide) was 98% and the selectivity of the reaction (based on the converted isophorone) was 98%.

EXAMPLE 8

The procedure of Example 1 was repeated, except that 8.7 g (0.033 mol) of tetra-n-propyl ammonium bromide was used in the place of tetraethyl ammonium bromide. The resultant reaction solution was subjected to after-treatment. When the organic layer consequently obtained was analyzed by gas chromatography, it was found to contain 111.4 g (0.674 mol) of 3-cyano-3,5,5-trimethyl cyclohexane and 40.4 g of an unaltered isophorone. Thus, the yield of 3-cyano-3,5,5-trimethyl cyclohexanone (based on hydrogen cyanide) was 96% and the selectivity of the reaction (based on the converted isophorone) was 95%.

EXAMPLE 9

The procedure of Example 1 was repeated, except that 11.1 g (0.033 mol) of tetra-n-butyl phosphonium bromide was used in the place of tetraethyl ammonium bromide and 27.0 g (1.0 mol) of hydrogen cyanide was additionally used. The resultant reaction solution was subjected to after-treatment. When the organic layer consequently obtained was analyzed by gas chromatography, it was found to contain 155.3 g (0.940 mol) of 3-cyano-3,5,5-trimethyl cyclohexanone. Thus, the yield of 3-cyano-3,5,5-trimethyl cyclohexanone (based on hydrogen cyanide) was 94%.

EXAMPLE 10

The procedure of Example 1 was repeated, except that 6.1 g (0.033 mol) of benzyltrimethyl ammonium chloride was used in the place of tetraethyl ammonium bromide. The resultant reaction solution was subjected to aftertreatment. When the organic layer consequently obtained was analyzed by gas chromatography, it was found to contain 109.1 g (0.660 mol) of 3-cyano-3,5,5-trimethyl cyclohexanone and 41.0 g of an unaltered isophorone. Thus, the yield of 3-cyano-3,5,5-trimethyl cyclohexanone (based on hydrogen cyanide) was 94% and the selectivity of the converted (based on the converted isophorone) was 94%.

EXAMPLE 11

The procedure of Example 1 was repeated, except that 6.9 g (0.065 mol) of sodium carbonate was used in the place of potassium carbonate. The resultant reaction solution was subjected to after-treatment. When the organic layer consequently obtained was analyzed by gas chromatography, it was found to contain 110.8 g (0.671 mol) of 3-cyano-3,5,5-trimethyl cyclohexanone as the product and 40.3 g of an unaltered isophorone. Thus, the yield of 3-cyano-3,5,5-trimethyl cyclohexanone (based on hydrogen cyanide) was 96% and the selectivity of the reaction (based on the converted isophorone) was 95%.

EXAMPLE 12

In the same apparatus as used in Example 1, 138.2 g (1.0 mol) of isophorone, 6.9 g (0.033 mol) of tetraethyl ammonium bromide, 6.9 g (0.069 mol) of potassium hydrogen carbonate, and 13.8 g of water were placed, stirred and heated to 105° C., 18.9 g (0.70 mol) of hydrogen cyanide was added dropwise thereto at a temperature of 105° C. over a period of three hours. After the addition, the reaction mixture was aged at 105° C. for one hour to complete the reaction. After the reaction was completed, the resultant reaction mixture was cooled to 50° C. The cooled reaction mixture and 70 g of water added thereto were stirred and left standing until phase separation. From the organic layer, the catalyst was separated. The organic layer was neutralized by being combined with 70 g of a 6% nitric acid solution, stirred, and left standing until phase separation. When the organic layer consequently obtained was analyzed by gas chromatography, it was found to contain 113.6 g (0.687 mol) of 3-cyano-3,5,5-trimethyl cyclohexanoneand and 39.9 g of unaltered isophorone. Thus, the yield of 3-cyano-3,5,5-trimethyl cyclohexanone (based on hydrogen cyanide) was 98% and selectivity of the reaction (based on the converted isophorone) was 97%.

EXAMPLE 13

The procedure of Example 1 was repeated, except that 9.7 g (0.070 mol) of potassium carbonate was used in the place of 6.9 g (0.050 mol) of potassium carbonate. The resultant reaction solution was subjected to aftertreatment. When the organic layer consequently obtained was analyzed by gas chromatography, it was found to contain 111.0 g (0.672 mol) of 3-cyano-3,5,5-trimethyl cyclohexanone as the product and 40.5 g of unaltered isophorone. Thus, the yield of 3-cyano-3,5,5-trimethyl cyclohexanone (based on hydrogen cyanide) was 96% and the selectivity of the reaction (based on the converted isophorone) was 95%.

EXAMPLE 14

The procedure of Example 1 was repeated, except that 4.1 g (0.030 mol) of potassium carbonate was used in the place of 6.9 g (0.050 mol) of potassium carbonate. The resultant reaction was subjected to after-treatment. When the organic layer consequently obtained was analyzed by gas chromatography, it was found to contain 113.4 g (0.686 mol) of 3-cyano-3,5,5-trimethyl cyclohexanone as the product and 41.6 g of unaltered isophorone. Thus, the yield of 3-cyano-3,5,5-trimethyl cyclohexanone (based on hydrogen cyanide) was 98% and the selectivity of the reaction (based on the converted isophorone) was 98%.

EXAMPLE 15

In a 1-m³ glass-lined reactor equipped with a reflux condenser and a hydrogen cyanide storage tank connected thereto, 390 kg (2.82 k.mols) of isophorone, 19 kg (0.09 k.mol) of tetraethyl ammonium bromide, 19 kg (0.14 k.mol) of potassium hydrogen carbonate, and 38 kg of water were placed, stirred and heated to 110° C. 52 kg (1.92 k.mols) of hydrogen cyanide was added dropwise thereto at a temperature of 108° to 112° C. over a period of three hours. After the addition, the reaction mixture was aged at 110° C. for one hour to complete the reaction. After the completion of this reaction, the resultant reaction mixture was cooled to 50° C. The reaction mixture and 200 kg of water added thereto were stirred and left standing until phase separation. From the organic layer, the catalyst was separated. Further, the organic layer was neutralized by being combined with 150 kg of a 6% nitric acid solution, stirred, and left standing until phase separation. When the organic layer consequently obtained was analyzed by gas chromatography, it was found to contain 311 kg (1.89 k.mols) of 3-cyano-3,5,5-trimethyl cyclohexanone and 121 kg of unaltered isophorone. Thus, the yield of 3-cyano-3,5,5-trimethyl cyclohexanone (based on hydrogen cyanide) was 98% and the selectivity of the reaction (based on the converted isophorone) was 97%. When the organic layer consequently obtained was distilled, there were obtained 101 kg of converted isophorone (comprising 99 kg of isophorone and 2 kg of 3-cyano-3,5,5-trimethyl cyclohexanone), 49 kg of a forerun (comprising 19 kg of isophorone and 30 kg of 3-cyano-3,5,5-trimethyl cyclohexanone), and 281 kg of 3-cyano-3,5,5-trimethyl cyclohexanone having a purity of 99%.

EXAMPLE 16

When the catalyst-containing aqueous layer obtained in Example 15 was analyzed, it was found to contain 16.4 kg of tetraethyl ammonium bromide and 16.8 kg of potassium carbonate. The recovery ratio based on the initially charged amount was 86% in the case of tetraethyl ammonium bromide and 88% in the case of potassium carbonate. In the same apparatus as used in Example 15, this aqueous layer concentrated to 77 kg, 101 kg of the isophorone (comprising 99 kg of isophorone and 2 kg of 3-cyano-3,5,5-trimethyl cyclohexane) recovered in Example 15, 281 kg of isophorone, 2.6 kg of tetraethyl ammonium bromide, and 2.2 kg of potassium carbonate were placed, stirred and heated to 110° C., 52 kg of hydrogen cyanide was added dropwise thereto at a temperature of 108° to 112° C. over a period of three hours. After the addition was completed, the reaction mixture was left aging at 110° C. for one hour to complete the reaction. After the reaction was completed, the reaction mixture was cooled to 50° C. The cooled reaction mixture and 200 kg of water added thereto were stirred and left standing until phase separation. From the organic layer, the catalyst was separated. The organic layer was neutralized by being combined with 150 kg of water, stirred, and left standing until phase separation. When the organic layer consequently obtained was analyzed by gas chromatography, it was found to contain 312 kg of 3-cyano-3,5,5-trimethyl cyclohexanone and 112 kg of unaltered isophorone. Thus, the yield of 3-cyano-3,5,5-trimethyl cyclohexanone minus the part originating from the recovered isophorone (based on hydrogen cyanide) was 98% and the selectivity of the reaction (based on the converted isophorone) was 97%. When the organic layer consequently obtained and 49 kg of the forerun (comprising 19 kg of isophorone and 30 kg of 3-cyano-3,5,5-trimethyl cyclohexanone) obtained in Example 15 were combined and distilled, there were obtained 108 kg of recovered isophorone (containing 106 kg of isophorone and 2 kg of 3-cyano-3,5,5-trimethyl cyclohexanone), 50 kg of a forerun (comprising 21 kg of isophorone and 29 kg of 3-cyano-3,5,5-trimethyl cyclohexanone), and 314 kg of 3-cyano-3,5,5-trimethyl cyclohexanone having a purity of 99%.

What is claimed is:

1. A method for the production of 3-cyano-3,5,5-trimethylcyclohexanone by the reaction of isophorone with hydrogen cyanide, in the presence of a quaternary ammonium salt or quaternary phosphonium salt represented by the following formula:

$$R^1(R^2)_3AX,$$

wherein $R^1$ is benzyl or alkyl of 1 to 4 carbon atoms, inclusive, $R^2$ is alkyl of 1 to 4 carbon atoms, inclusive, A is nitrogen or phosphorus, and X is chlorine, bromine, or iodine, and a basic compound selected from the group consisting of sodium carbonate, potassium carbonate, sodium hydrogen carbonate, and potassium hydrogen carbonate as a catalyst dissolved or dispersed in water, or in the absence of water, which method comprises effecting said reaction:

by using said quaternary ammonium salt or quaternary phosphonium salt in an amount in the range of 0.02 to 0.07 mol per mol of isophorone;

by using said basic compound in an amount in the range of 0.5 to 3.0 mols per mol of said quaternary ammonium salt or quaternary phosphonium salt;

by employing hydrogen cyanide at a ratio in the range of 0.6 to 1.0 mol per mol of isophorone at a temperature in the range of 100° to 130° C.;

and, when water is used, using water in an amount in the range of 0.1 to 25% by weight based on the amount of isophorone.

2. A method according to claim 1, which further comprises allowing the resultant reaction solution to be separated by contact with water into an organic layer and an aqueous layer containing said quaternary ammonium salt or quaternary phosphonium salt and said basic compound used in said reaction, and recovering from said aqueous layer said quaternary ammonium salt or quaternary phosphonium salt and said basic compound, and putting the recovered catalyst to reuse in the next cycle of the reaction.

3. A method according to claim 1, wherein said quaternary ammonium salt is at least one member selected from the group consisting of chlorides and bromides of tetramethyl ammonium, tetraethyl ammonium, and methylethyl ammonium.

4. A method according to claim 1, wherein the time for the introduction of hydrogen cyanide is in the range of 1 to 7 hours.

5. A method according to claim 1, wherein said reaction is carried out in the absence of an organic solvent.

* * * * *

UNITED STATES PATENT AND TRADEMARK OFFICE
CERTIFICATE OF CORRECTION

PATENT NO. : 5,179,221
DATED : January 12, 1993
INVENTOR(S) : Hiroshi Takahoso, et. al.

It is certified that error appears in the above-indentified patent and that said Letters Patent is hereby corrected as shown below:

Title page, item [73] Assignee: "Nippon" should read -- Nippoh --.

Signed and Sealed this

Eleventh Day of July, 1995

Attest:

BRUCE LEHMAN

Attesting Officer

Commissioner of Patents and Trademarks